United States Patent [19]

Buchanan et al.

[11] Patent Number: 5,668,017
[45] Date of Patent: Sep. 16, 1997

[54] RADIAL ABSORPTION DEVICE

[75] Inventors: Ian Ellis Buchanan, Kirkland; Milton Richard Tam, Seattle, both of Wash.

[73] Assignee: Path, Seattle, Wash.

[21] Appl. No.: 386,650

[22] Filed: Feb. 10, 1995

[51] Int. Cl.[6] .................. G01N 21/00; G01N 31/22; G01N 33/53; G01N 33/543
[52] U.S. Cl. .................. 436/518; 436/169; 436/528; 436/538; 436/524; 436/807; 436/809; 435/7.91; 435/287.1; 435/287.7; 435/287.9; 435/810; 435/970; 422/56; 422/57; 422/58; 422/60; 422/68.1; 422/99; 422/101
[58] Field of Search .................. 422/56, 57, 58, 422/60, 68.1, 99, 101, 274, 275, 276, 277; 435/7.91, 6, 7.92, 7.93, 7.94, 970, 810, 287.1–287.2, 287.7, 287.9, 288.4; 436/518, 169, 528, 807, 538, 809, 534

[56] References Cited

U.S. PATENT DOCUMENTS

| | | |
|---|---|---|
| 3,526,480 | 9/1970 | Findl et al. |
| 3,607,079 | 9/1971 | Maxon .................. 23/230 R |
| 4,071,315 | 1/1978 | Chateau .................. 23/230 B |
| 4,618,475 | 10/1986 | Wang .................. 422/56 |
| 4,623,461 | 11/1986 | Hossom et al. .................. 210/445 |
| 4,767,702 | 8/1988 | Cohenford .................. 435/24 |
| 4,837,373 | 6/1989 | Gunkel et al. .................. 422/56 |
| 4,900,663 | 2/1990 | Wie et al. .................. 435/7 |
| 4,938,927 | 7/1990 | Kelton et al. .................. 422/64 |
| 4,956,302 | 9/1990 | Gordon et al. .................. 436/56 |
| 5,141,875 | 8/1992 | Kelton et al. .................. 436/514 |
| 5,202,268 | 4/1993 | Kuhn et al. .................. 436/525 |
| 5,207,984 | 5/1993 | Kheiri .................. 422/58 |
| 5,209,904 | 5/1993 | Forney et al. .................. 422/73 |

*Primary Examiner*—Christopher L. Chin
*Assistant Examiner*—Bao-Thuy L. Nguyen
*Attorney, Agent, or Firm*—Banner & Witcoff, Ltd.

[57] ABSTRACT

The assay device of this invention provides for very simple assay procedures leading to rapid, sensitive, specific detection of an analyte in a solution. The device is inexpensive and easily manufactured, particularly if automated manufacturing processes are used. The assay device is a test strip having an elongated support sheet of solid non-porous material attached to a similarly shaped sheet of absorbent material. The absorbent sheet has perforations, preferably of circular shape, forming sample receiving wells. Forming the bottom of the sample receiving wells is one surface of the support sheet, and attached to this surface are moieties which specifically bind the analyte (anti-analyte moieties). A liquid sample for assay is placed in the wells, and the liquid is drawn into the absorbent material. As the liquid is absorbed, it flows tangentially across the surface of the support sheet, and across binding moieties specific for the analyte which are attached to the bottom of the wells. If analyte is present in the sample, analyte will form a complex with anti-analyte attached to the support surface, and detection of the complex will demonstrate the presence of the analyte.

16 Claims, 2 Drawing Sheets

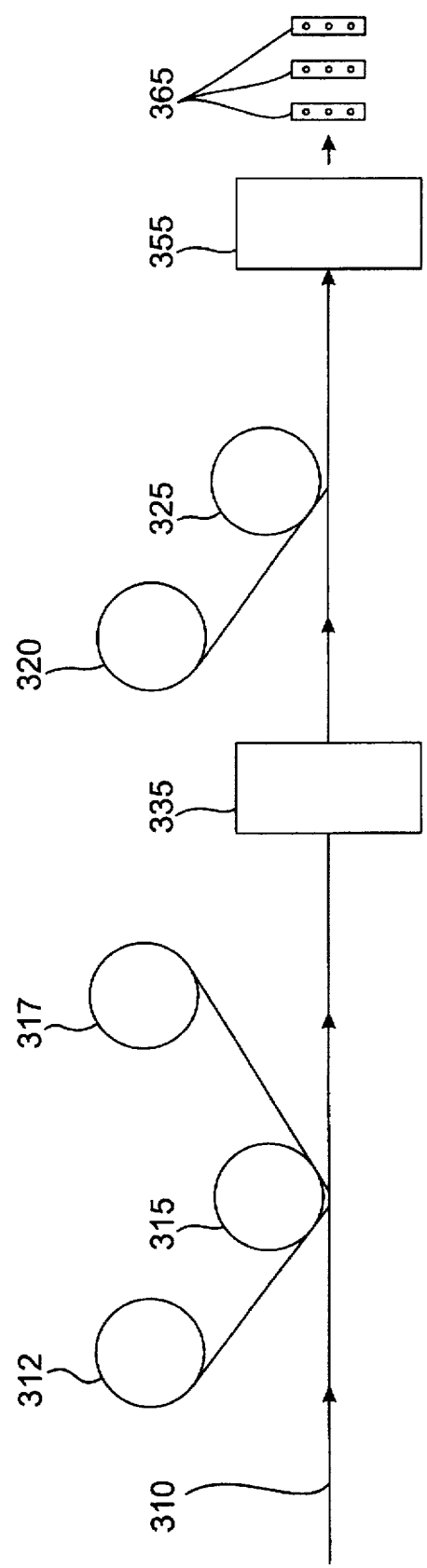

RADIAL ABSORPTION DEVICE

BACKGROUND OF THE INVENTION

The invention relates to test strips for the detection of analytes in liquids. More particularly, the invention relates to assay devices made up of moieties that bind specifically to a particular analyte, a support substrate to which the moieties are attached, and at least one absorbent matrix laminated to the support substrate that promotes the flow of liquid across the attached moieties.

RELATED ART

Various assay devices are known in the art for use in detecting substances in solution. In particular, such devices may be in the form of dipsticks for dipping into a solution or test cards on which a sample of solution is placed. In either case, if the substance (i.e., the analyte) is present in the solution, a test zone of the device displays some detectable change, such as a color change. A variant of the test card is a test strip, a long strip on which the test zone is repeated, and separate samples may be applied to successive test zones mechanically, thus automating the assay.

Test strips have been used for a long time for qualitative detection of various substances in solution and also, to an increasing extent, in combination with evaluation devices, for the quantitative detection of such substances. Test strips of this type consist, as a rule, of an elongated plastic sheet with matrices or reaction zones fastened thereto in the form of papers impregnated with reagents, films coated with reagents or special layers containing the reagent.

U.S. Pat. No. 4,618,475 discloses a reagent test stick device or dipstick made up of an elongated plastic substrate to which alternating reagent pads (porous material impregnated with reagents for detection of particular analytes) and barrier pads (hydrophobic material that prevents liquid transport from one reagent pad to another) are attached. When the reagent test stick is dipped in a sample solution, the sample solution is absorbed into the various alternating reagent pads and the test reagents on the reagent pads react with their respective analytes, providing for determination of multiple analytes in a single procedure.

U.S. Pat. No. 4,837,373 also discloses test strips in the form of dipsticks made up of a firm support to which is attached a series of adhesive strips placed 0.5–3 mm apart, with absorbent matrices between the adhesive strips, by which the absorbent material is fixed in position on the firm support. The absorbent matrices are impregnated with reagents for detection of particular analytes. When the test strip is dipped into a sample, the sample solution is absorbed by the matrices, where any analyte in the sample reacts with the reagents. Preferably, the reagent matrices on the test strip are covered by a film with circular, well-like openings.

U.S. Pat. No. 4,767,702 discloses a test card device made up of a strip of filter paper containing three test areas which are accessible through three circular openings in a cover encasing the filter paper.

U.S. Pat. Nos. 4,900,663 and 5,240,844 disclose test card devices having test ports communicating with antigen binding substrate on a porous matrix communicating in turn with a fluid reservoir made up of a filter body such that sample introduced into the test port will flow through to the fluid reservoir.

U.S. Pat. Nos. 4,938,927 and 5,141,875 describe test cards in which fluid flow is through a porous body is controlled by directing the fluid through slots or between lines of reduced porosity formed by localized compaction. U.S. Pat. No. 5,202,268 also teaches a test card which uses multiple layers of varying porosity to direct flow of liquid through a test card.

U.S. Pat. No. 5,207,984 shows a test strip with a sample application site defined by a collar-like, plastic body which directs an applied sample into the reagent test zone.

U.S. Pat. Nos. 3,526,480 and 3,607,079 pertain to automated chemical analysis apparatus which use continuous, tape-like, test strips. U.S. Pat. No. 4,071,315, which is also directed to an analytical tape for use in automated analysis apparatus, discloses the use of polystyrene or polypropylene films and transverse tear-off lines.

However, while the devices disclosed in the prior art are useful in the specific analytical situations taught, there remains a need for a test device that is rapid, sensitive, specific, simple-to-use, and very inexpensive to manufacture.

SUMMARY OF THE INVENTION

It is an object of this invention to provide an improved test strip apparatus for use in detection of a particular analyte in a fluid sample, including analytical zones for receiving sample which contain anti-ligand moieties to specifically bind any of the analyte in the sample for subsequent detection of bound analyte.

It is a further object of this invention to provide an easily manufactured test strip apparatus for use in an automated analytical apparatus.

It is yet another object of this invention to provide an assay method for determining the presence of an analyte in a fluid sample using an improved test strip apparatus, including analytical zones for receiving sample which contain anti-ligand moieties to specifically bind any analyte in the sample for subsequent detection of bound analyte. These and other objects are met by one or more of the following embodiments of this invention.

In one embodiment, this invention provides a test strip apparatus for use in detection of an analyte in a fluid sample, the test strip including an upper strip of absorbent material, preferably fiberboard, and a lower strip of non-porous material, preferably polystyrene, the upper strip being laminated to an upper surface of the lower strip. The test strip includes a plurality of wells adapted to receive a fluid sample, a well being a transverse hole, preferably of circular shape, piercing the upper strip such that a fluid sample placed in the well is in contact with an area of the upper surface of the lower strip, at least a portion of the area of the upper surface of the lower layer which is in contact with the fluid sample being coated with anti-analyte moieties which specifically bind the analyte, whereby when the fluid sample is introduced into the well, the fluid sample will be absorbed into the absorbent material so that the fluid flowing into the absorbent layer will flow laterally over the upper surface of the lower layer and the anti-analyte moieties coating it. The analyte/anti-analyte according to this invention are preferably an antigen-antibody pair or a nucleic acid and its complement. In a particularly preferred embodiment, the analyte is an antibody and the anti-analyte is an antigen recognized by the antibody.

In a preferred embodiment, the test strip apparatus of this invention further includes score lines placed between adjacent sample receiving wells to demarcate individual test wells. These score lines may include perforations which facilitate breaking the test strip between adjacent wells.

In another preferred embodiment, the test strip apparatus of this invention further contains means for controlling flow rate of fluid from the well into the absorbent material. The means for controlling flow rate may be a ring of the absorbent material adjacent to the well, the material in the ring having increased density resulting from compression of the absorbent material. Alternatively, the means for controlling flow rate may be a ring of absorbent material adjacent to the well with additional soluble material, such as gelatin or starch, dried therein. In another alternative, the means for controlling flow rate may be a lining of non-porous material in contact with the ring of absorbent material forming the wall of the sample receiving well, the non-porous lining containing a plurality of perforations through which fluid of the sample may pass from the well into the absorbent material.

In another embodiment, this invention provides an assay method for determining the presence of an analyte in a fluid sample, comprising placing a fluid sample in a well in an test strip assay device, the well including a transverse hole in an upper layer of absorbent material laminated to an upper surface of a lower layer of non-porous material, the well traversing the absorbent layer to permit the fluid sample to directly contact the upper surface of the non-porous layer, at least a portion of the upper surface of the non-porous layer within the well being coated with anti-analyte moieties which specifically bind the analyte, allowing the absorbent material of the upper layer to absorb the fluid sample, whereby the fluid sample flows laterally over the upper surface of the lower non-porous layer and analyte/anti-analyte complex forms between the anti-analyte moieties coating the upper surface of the lower non-porous layer and analyte in the fluid, and detecting analyte/anti-analyte complex. In a particularly preferred embodiment, the hole in the upper strip is circular and the fluid sample flows radially over the upper surface of the lower non-porous layer. Preferably, the analyte and the anti-analyte of this assay method comprise an antigen-antibody pair or a nucleic acid sequence and its complement. In a particularly preferred embodiment, the analyte is an antibody and the anti-analyte is an antigen recognized by the antibody.

The assay device of this invention allows analyte solution placed in the sample receiving wells to flow tangentially across the surface on which the anti-analyte is immobilized and into the absorbent sheet surrounding the well. The principle behind the assay device according to this invention thereby differs from the principle used by other immunoconcentration devices which allow for a flow of the analyte through a permeable membrane and into an absorbent pad. The rapid flow of the analyte over the solid phase support created by absorption may generate turbulence, which allows for accelerated binding of antigen or antibody from the analyte.

Another unique feature of the device is the potential for control of fluid absorption by the fiberboard by means of either altering the density of the fiberboard in the absorptive region by compression/crimping in a limited area, or by depositing and drying a soluble substance such as gelatin. Another method of controlling flow is to add a simple plastic "collar" to the well containing perforations which control the flow. One or a combination of methods may be used to first retain and then control the flow of analyte solution.

BRIEF DESCRIPTION OF THE DRAWINGS

FIG. 3 shows a schematic representation of a manufacturing process for production of the assay device of this invention.

DETAILED DESCRIPTION OF THE EMBODIMENTS

The present invention provides a novel assay device, which can be used for detection of one or more analytes. The assays performed with the assay device of this invention are based on specific binding between an analyte and an anti-analyte moiety. Typically, the analyte/anti-analyte will be an antigen-antibody pair, but the skilled worker will be aware of other ligand binding pairs of similar specificity that may also be used, such as a nucleic acid and its complement. Any ligand binding pair may be used, so long as the binding reaction occurs with rapidity and specificity similar to that of antigen-antibody binding or nucleic acid hybridization.

The assay devise of this invention provides for very simple assay procedures leading to rapid, sensitive, specific detection of an analyte in a solution. The device is inexpensive and easily manufactured, particularly if automated manufacturing processes are used. The assay device is a test strip having an elongated support sheet of solid non-porous material attached to a similarly shaped sheet of absorbent material. The absorbent sheet has perforations, preferably of circular shape, forming sample receiving wells. Forming the bottom of the sample receiving wells is one surface of the support sheet, and attached to this surface are moieties which specifically bind the analyte (anti-analyte moieties). A liquid sample for assay is placed in the wells, and the liquid is drawn into the absorbent material. As the liquid is absorbed, it flows tangentially across the surface of the support sheet, and across binding moieties specific for the analyte which are attached to the bottom of the wells. If analyte is present in the sample, analyte will form a complex with anti-analyte attached to the support surface, and detection of the complex will demonstrate the presence of the analyte.

In particular embodiments, analyte flow along the fiberboard is controlled by localized crimping of the fiberboard, increasing its density, or by use of plastic collars or by deposit, and subsequent drying, of a soluble substance such as gelatin in the fiberboard. In some embodiments, the strip will be provided in a long continuous form and will have perforations for tearing off individual test sites.

Structure of the Assay Device

Figure 1A:
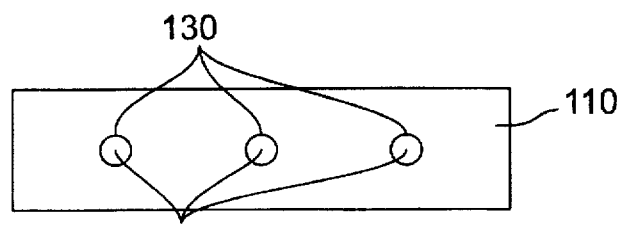
FIG. 1 shows three views of one embodiment of the test strip according to this invention. A is a top view; B is a side view; and C is a perspective view.
Figure 1B:
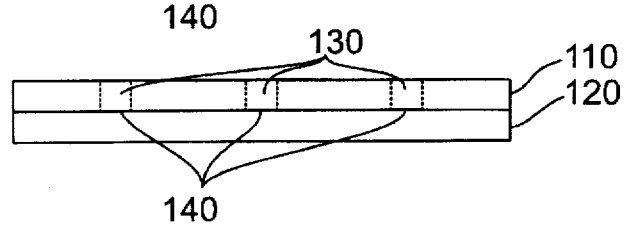
Figure 1C:
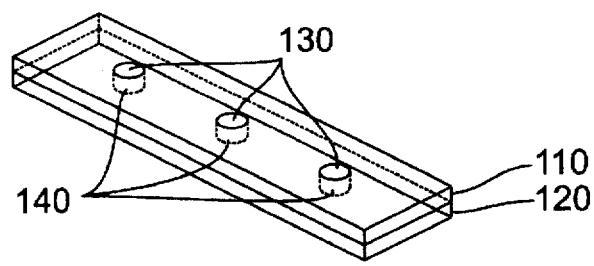

The device of this invention may be described by reference to a typical embodiment shown in FIG. 1, which shows a sheet of absorbent material 110 laminated to a non-porous support sheet 120.

Absorbent sheet 110 is made of, for example, filter paper, nonwovens, fabrics made from natural or synthetic fibers, porous gels or laminations of these materials. Other suitable materials include felt, porous ceramic material and woven or matted glass fibers taught in U.S. Pat. No. 3,846,247. Alternatively, absorbent material 110 may be wood, cloth, sponge material and argillaceous substances taught in U.S. Pat. No. 3,552,928, or synthetic resin fleeces in glass fiber felts as suggested in British Pat. No. 1,369,139, or a light permeable meshwork of thin filaments as suggested in British Pat. No. 1,349,623. Also suitable are polyamide fibers are taught in French Pat. No. 2,170,397. Notwithstanding these suggestions, however, the material preferred for use as the absorbent material of this invention is fiberboard, matboard, or a layer of bibulous paper, such as filter paper.

The porosity or absorbency of the absorbent material is selected with consideration of the length of time required for reaction between the analyte and the anti-analyte. Where the reaction is rapid, the absorbent material may be highly porous to facilitate completion of the assay in shorter time. Where the reaction is slow, porosity will be limited to increase the time required for the liquid in the sample to be drawn into the absorbent material, thereby increasing the time for reaction between the analyte and the anti-analyte. Methods of controlling porosity during manufacture of the absorbent material or manufacture of the assay device will be apparent to the skilled worker in view of the preceding description.

The substrate 120 can be formed from any suitable material including polystyrene, polyvinylchloride, polyethylene, polycarbonate, polyesters or polyamides, etc. However, supports composed of metal films, for example aluminum, or supports composed of glass are also suitable. Preferably the substrate 120 is flexible to facilitate manufacture of the test strip and/or use in an automated analysis apparatus, such as that described in U.S. Pat. Nos. 3,526,480 or 3,607,079. A preferred material is polystyrene of food or pharmaceutical grade, such as Mobil 4600A Food Grade Polystyrene extruded to 15 mil thickness.

Absorbent sheet 110 is typically attached to the supporting substrate sheet 120 by glue or adhesive. The glue or adhesive material employed to bind the absorbent sheet to substrate 120 can be any suitable material which is capable of bonding the absorbent sheet to the substrate and readily adhering the different materials together. Double backed adhesive tape known a Double-Stick, available from the 3M Company, is suitable. A preferred adhesive is product #9875 from 3M Medical Specialties, which is a pressure sensitive acrylate adhesive provided in pharmaceutical grade as a 1.8 mil strip on #60 liner (a silicone treated bleached Kraft Glassine paper).

The assay device contains one or more sample receiving wells 130, which are perforations in the absorbent sheet 110 that provide access to a surface area 40 of the support sheet 120. Preferably, the perforations are circular in shape, so that the fluid in a sample placed into the well will flow radially into the absorbent material surrounding the receiving well. In alternative embodiments, the assay device has more or fewer sample receiving wells, which are usually provided by extending the elongated support sheet and the absorbent sheet laminated thereto. In a particularly preferred embodiment, the assay device is a test strip having regularly spaced sample receiving wells for use as a tape in an automated assay machine, similar to the analysis apparatus taught in U.S. Pat. Nos. 3,526,480 or 3,607,079.

Anti-analyte is attached to the surface area 140 of the support sheet. The procedure for attaching the anti-analyte will depend on the chemical nature of the anti-analyte and the non-porous substrate. These procedures are well known, and selection of a suitable procedure is within the skill of the art. In a preferred embodiment, anti-analyte is attached to only a portion of surface area 140. In one preferred embodiment, two or more anti-ligands specific for two or more analytes are attached to two or more separate portions of surface area 140, respectively. The test device of this embodiment can be used to detect, in the same sample, the presence of any one or all of the analytes which bind the two or more anti-analytes. Alternatively, one portion of surface area 140 may represent a control, wherein the control portion of surface area 140 is coated with a moiety which specifically binds a ligand that is present in every sample.

In one preferred embodiment, the assay device of this invention is a test strip assembled from polystyrene plastic sheeting laminated to a fiberboard sheet of similar size. A circular perforation or "well" is made in the fiberboard to allow access to the plastic sheet, onto which one or more antigens or capture antibodies in individual or multiple spots is immobilized. An additional spot which can serve as a positive control can be added as distinct from the test spots.

Figure 2A:
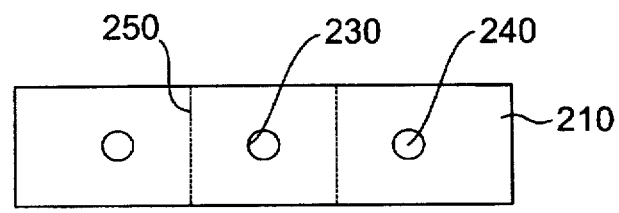
FIG. 2A–C shows the same three views of an alternative embodiment of this invention.
Figure 2B:
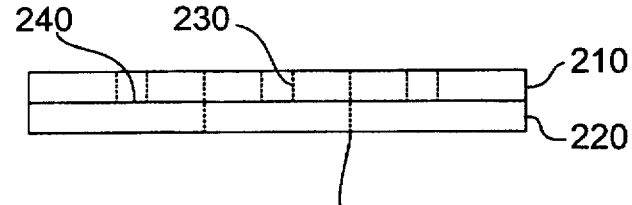
Figure 2C:
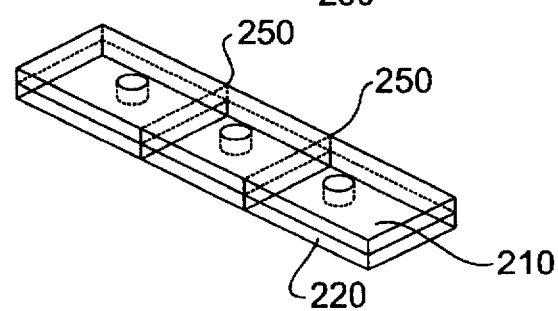

While tests would preferably be run on long strips with regularly spaced receiving wells using automated equipment, it may be desirable to break off individual test spot units for placing in separate patient files. In another preferred embodiment, shown in FIG. 2, perforations or score lines 250 are placed between the test spots so that the units can be easily separated.

Assay devices according to this invention are particularly well adapted to manufacture on high speed machines. FIG. 3 is a schematic representation of such a manufacturing process, which is described in the following Example.

EXAMPLE

Regular matboard, such as that available in sheets of 36"×48" from art supply stores, is contacted with 3M Medical Specialties product reference grade 1.8 mil pressure transfer adhesive #9875 backed with Kraft Glassine paper. FIG. 3 shows the path of travel for the matboard 310 which contacts the transfer adhesive 312 under a pressure roller 315. After the adhesive is applied to the matboard, the backing is removed. In FIG. 3, the backing is taken up by take-up roll 317. A punch 335 then punches holes of 5/16" diameter in the sheet plus adhesive, positioned on 1" centers. The size and spacing of the holes may vary depending on the absorbency and liquid holding capacity of the matboard. The substrate 320, a sheet of 15 mil polystyrene, is applied to the exposed adhesive under a second pressure roller 325, and strips containing multiple holes are cut from the sheet with, for example, a guillotine cutter 355, to produce the individual assay device 365. Alternative arrangements for manufacture of the assay device will be readily apparent to those skilled in the art.

Use of the Assay Device

Examples of specimens which can be used with the device include serum, plasma, whole blood treated with anticoagulant, urine, saliva, vaginal and cerebrospinal fluids. Assays using the device of this invention are performed by placing a fluid sample of the solution to be tested in the receiving well of the test strip assay device, and allowing the material of the absorbent sheet surrounding the well to absorb the fluid in the sample. As fluid flows laterally over the upper surface of the non-porous layer which forms the base of the well, analyte/anti-analyte complex forms between the anti-analyte moieties coating the bottom of the well and any analyte in the fluid. In a particularly preferred embodiment, the sample receiving well in the upper strip of absorbent material is circular and flow of the fluid sample over the upper surface of the lower non-porous layer is radial.

After the sample liquid is absorbed by the absorbent sheet, one or more signal reagents may then be used to visualize the analyte/anti-analyte complex formed by reaction of any analyte present in the sample. Suitable signal reagents will be readily apparent to the skilled worker, including but not limited to metallic sol particles, carbon sol particles, magnetic (ferrous) beads, latex beads, enzyme-labelled antigen/antibody/other substances having an affinity for the captured analyte (ELISA system). A common example we have used is colloidal gold conjugated with protein A, a bacterial protein.

In a preferred embodiment, the device of this invention is used for immunoassay where the analyte/anti-analyte combination is an antigen-antibody pair. Examples of immunoassays which can utilize the device of the invention are competitive and non-competitive immunoassays in either a direct or indirect format. The device of the invention can be utilized with immunoassays which run in either the forward, reverse, or simultaneous modes, including radioimmunoassay (RIA) and the sandwich (immunometric) assay.

The assay device of this invention may also be used for nucleic acid (NA) hybridization assays. In this application, specific NA fragments are immobilized to the plastic surface. The extracted NA from the specimen, either with or without prior amplification with techniques such as PCR, is applied to the well. After absorption of the analyte, signal reagent such as avidin or monoclonal antibody specific to NA duplexes or haptens conjugated to signal, for example horseradish peroxidase enzyme, is added. This is followed by development with a chromogenic substrate which produces a characteristic color and precipitates over the area of reaction.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the invention as disclosed herein. Modifications of the above-described modes for carrying out the invention that are obvious to persons of skill in medicine, immunology, hybridoma technology, pharmacology, and/or related fields are intended to be within the scope of the following claims.

We claim:

1. A test strip apparatus for use in detection of an analyte in a fluid sample by immunoassay, including:

an upper strip of absorbent material, and a lower strip of non-porous material, the upper strip being laminated to an upper surface of the lower strip, the test strip including a plurality of wells for receiving a fluid sample, a well being a transverse hole piercing the absorbent material of the upper strip such that the upper surface of the lower strip forms a base of the well, wherein at least a portion of the base of the well is coated with anti-analyte moieties which specifically bind the analyte, such that a fluid sample placed into the well is in direct contact with the anti-analyte moieties and fluid flows into the absorbent material radially away from the anti-analyte moieties on the base of the well.

2. The test strip of claim 1 wherein the anti-analytes are nucleic acid probes.

3. A test strip apparatus according to claim 1, wherein the analyte and the anti-analyte comprise an antigen-antibody pair.

4. The test strip apparatus of claim 1, wherein the non-porous material is polystyrene plastic sheeting.

5. The test strip apparatus of claim 1, wherein the absorbent material is fiberboard.

6. The test strip apparatus of claim 1, wherein the hole in the upper strip is circular.

7. The test strip apparatus of claim 1, further including score lines placed between adjacent wells to demarcate individual test wells.

8. The test strip apparatus of claim 7, wherein the score lines include perforations which facilitate breaking the test strip between adjacent wells.

9. The test strip apparatus of claim 1, further containing means for controlling flow rate of fluid from the well into the absorbent material.

10. The test strip apparatus of claim 9, wherein the absorbent material is compressed to form a ring of the absorbent material adjacent to the well, said ring having an increased density relative to the remainder of the upper strip, which ring is the means for controlling flow rate.

11. The test strip apparatus of claim 9, wherein the means for controlling flow rate is a ring of absorbent material with additional soluble material dried therein adjacent to the well.

12. The test strip apparatus of claim 9, wherein the means for controlling flow rate is a liner of non-porous material lining the well, the liner forming a ring in contact with the upper strip of absorbent material, the liner containing a plurality of perforations through which fluid may pass from the well into the absorbent material.

13. An assay method for determining the presence of an analyte in a fluid sample, comprising:

placing a fluid sample in a well in a test strip assay device, the well including a transverse hole in an upper layer of absorbent material laminated to an upper surface of a lower layer of non-porous material, the well traversing the absorbent layer to permit the fluid sample to directly contract the upper surface of the non-porous layer, at least a portion of the upper surface of the non-porous layer within the well being coated with anti-analyte moieties which specifically bind the analyte, allowing the absorbent material of the upper layer to absorb the fluid sample, whereby the fluid sample flows radially over the upper surface of the lower non-porous layer and an analyte/anti-analyte complex forms between the anti-analyte moieties coating the upper surface of the lower non-porous layer and analyte in the fluid, placing a signal reagent in the well, said reagent having an affinity for the analyte, and detecting the analyte/anti-analyte complex within the well by detecting a signal generated by the signal reagent, the presence of said signal within the well indicating the presence of the analyte in the fluid sample.

14. The assay method of claim 13, wherein the hole in the upper strip is circular.

15. The assay method of claim 13, wherein the analyte and the anti-analyte comprise an antigen-antibody pair.

16. The assay method of claim 13, wherein the analyte and the anti-analyte comprise a nucleic acid sequence and its complement.

* * * * *